(12) United States Patent
Mewissen et al.

(10) Patent No.: US 11,883,616 B2
(45) Date of Patent: Jan. 30, 2024

(54) MULTI-LUMEN INTRAVASCULAR CATHETERS WITH INNER CONVERGING LUMENS FOR MULTIPLE GUIDEWIRE CONTROL

(71) Applicant: Mekal, LLC, Franklin, WI (US)

(72) Inventors: Mark W. Mewissen, Franklin, WI (US); James R. Watson, Santa Rosa, CA (US)

(73) Assignee: Mekal, LLC, Franklin, WI (US)

( * ) Notice: Subject to any disclaimer, the term of this patent is extended or adjusted under 35 U.S.C. 154(b) by 0 days.

(21) Appl. No.: 17/688,007

(22) Filed: Mar. 7, 2022

(65) Prior Publication Data

US 2023/0011262 A1  Jan. 12, 2023

Related U.S. Application Data

(63) Continuation-in-part of application No. 17/369,008, filed on Jul. 7, 2021, now abandoned.

(51) Int. Cl.
*A61M 25/09* (2006.01)
*A61B 17/22* (2006.01)
(Continued)

(52) U.S. Cl.
CPC ....... *A61M 25/09041* (2013.01); *A61B 17/22* (2013.01); *A61M 25/003* (2013.01);
(Continued)

(58) Field of Classification Search
CPC .......... A61M 25/09041; A61M 25/003; A61M 25/0052; A61M 25/0068; A61M 25/0108;
(Continued)

(56) References Cited

U.S. PATENT DOCUMENTS 3,459,184 A  8/1969  Ring
4,306,562 A  12/1981  Osborne
(Continued)

OTHER PUBLICATIONS

"Substantial." Merriam-Webster.com Dictionary, Merriam-Webster, https://www.merriam-webster.com/dictionary/substantial. Accessed Feb. 1, 2023.*
(Continued)

*Primary Examiner* — Brooke Labranche
*Assistant Examiner* — Lauren Dubose
(74) *Attorney, Agent, or Firm* — Jansson Munger; McKinley & Kirby Ltd.

(57) ABSTRACT

In a multiple-lumen catheter having multiple guidewires for treatment of vascular blockages, the catheter comprising a proximal-end assembly, a distal-end portion and a multi-lumen medial portion therebetween, the improvement wherein: (1) the multiple guidewires are preloaded in the catheter, each guidewire in its own single-guidewire lumen extending from its own guidewire entry port in the proximal-end assembly to a lumen convergence portion; and (2) the distal-end portion includes: (a) the lumen convergence portion along which the multiple lumens merge into a single output lumen sized to match the largest-diameter lumen of the multiple lumens, (b) an intermediate distal-end section connected to the lumen convergence portion and surrounding the single output lumen continuing therethrough, and (c) a tapered tip surrounding the single output lumen continuing therethrough.

17 Claims, 11 Drawing Sheets

(51) Int. Cl.
  *A61M 25/00* (2006.01)
  *A61M 25/01* (2006.01)
  *A61B 17/00* (2006.01)

(52) U.S. Cl.
  CPC .... *A61M 25/0052* (2013.01); *A61M 25/0068* (2013.01); *A61M 25/0108* (2013.01); *A61B 2017/00778* (2013.01); *A61B 2017/22081* (2013.01)

(58) Field of Classification Search
  CPC .. A61M 2025/0031; A61M 2025/0037; A61M 25/0029; A61M 25/0097; A61M 25/0028; A61M 25/0071; A61M 25/0014; A61B 17/22; A61B 2017/22081
  USPC ........................................................ 604/284
  See application file for complete search history.

(56) References Cited

U.S. PATENT DOCUMENTS

| | | |
|---|---|---|
| 4,484,585 A | 11/1984 | Baier |
| 4,493,696 A | 1/1985 | Uldall |
| 4,641,912 A | 2/1987 | Goldenberg |
| 4,769,005 A | 9/1988 | Ginsburg et al. |
| 4,960,411 A | 10/1990 | Buchbinder |
| 4,968,307 A | 11/1990 | Dake et al. |
| 5,195,962 A | 3/1993 | Martin et al. |
| 5,203,338 A | 4/1993 | Jang |
| 5,219,335 A | 6/1993 | Willard et al. |
| 5,221,255 A * | 6/1993 | Mahurkar .......... A61M 25/0028 604/524 |
| 5,292,305 A * | 3/1994 | Boudewijn ....... A61M 25/0009 604/533 |
| 5,320,605 A | 6/1994 | Sahota |
| 5,397,302 A | 3/1995 | Weaver et al. |
| 5,458,584 A | 10/1995 | Ginn et al. |
| 5,531,700 A | 7/1996 | Moore et al. |
| 5,620,417 A | 4/1997 | Jang et al. |
| 5,830,196 A * | 11/1998 | Hicks ................ A61M 25/0029 604/523 |
| 5,935,114 A | 8/1999 | Jang et al. |
| 6,117,128 A * | 9/2000 | Gregory ................. A61B 18/24 606/7 |
| 6,120,516 A | 9/2000 | Selmon et al. |
| 6,241,744 B1 * | 6/2001 | Imran .................. A61B 8/0833 606/167 |
| 6,290,668 B1 * | 9/2001 | Gregory ............. A61M 25/003 604/510 |
| 6,394,141 B2 | 5/2002 | Wages et al. |
| 6,494,846 B1 | 12/2002 | Margolis |
| 6,524,302 B2 | 2/2003 | Kelley |
| 6,689,157 B2 | 2/2004 | Madrid et al. |
| 6,730,037 B2 | 5/2004 | Jang |
| 6,746,466 B2 | 6/2004 | Eidenschink et al. |
| 6,849,077 B2 | 2/2005 | Ricci |
| 6,976,991 B2 | 12/2005 | Hebert et al. |
| 7,001,358 B2 | 2/2006 | Fitzmaurice et al. |
| 7,018,358 B2 | 3/2006 | Joergensen et al. |
| 7,204,831 B2 | 4/2007 | Mcguckin, Jr. et al. |
| 7,229,429 B2 | 6/2007 | Martin et al. |
| 7,846,127 B2 | 12/2010 | Igarashi et al. |
| 7,875,019 B2 | 1/2011 | Barron et al. |
| 7,901,395 B2 | 3/2011 | Borden et al. |
| 7,981,093 B2 | 7/2011 | Schon et al. |
| 8,104,483 B2 | 1/2012 | Taylor |
| 8,137,336 B2 | 3/2012 | Ostrovsky et al. |
| 8,162,891 B2 | 4/2012 | Carley |
| 8,206,370 B2 | 6/2012 | Von Oepen et al. |
| 8,562,566 B2 | 10/2013 | Weber et al. |
| 8,617,231 B2 | 12/2013 | Vardi et al. |
| 8,628,519 B2 | 1/2014 | Taylor et al. |
| 8,728,011 B2 | 5/2014 | Khoury |
| 8,764,730 B2 | 7/2014 | Taber |
| 8,801,691 B2 | 8/2014 | Carley |
| 9,125,683 B2 | 9/2015 | Farhangnia et al. |
| 9,126,020 B2 | 9/2015 | Farhangnia et al. |
| 9,358,037 B2 | 6/2016 | Farhangnia et al. |
| 9,387,304 B2 | 7/2016 | Zawacki et al. |
| 9,526,874 B2 * | 12/2016 | Teeslink ........... A61B 17/12109 |
| 9,579,485 B2 | 2/2017 | Oborn et al. |
| 9,931,166 B2 | 4/2018 | Sauro et al. |
| 10,130,385 B2 | 11/2018 | Farhangnia et al. |
| 10,130,795 B2 | 11/2018 | Farhangnia et al. |
| 10,426,510 B2 | 10/2019 | Farhangnia et al. |
| 10,471,234 B2 | 11/2019 | Taber |
| 10,518,064 B2 | 12/2019 | Oborn et al. |
| 10,716,690 B2 | 7/2020 | Joye et al. |
| 11,058,849 B2 | 7/2021 | Schon et al. |
| 2004/0098087 A1 | 5/2004 | Madrid et al. |
| 2004/0220473 A1 * | 11/2004 | Lualdi ............... A61M 25/0172 604/529 |
| 2008/0082049 A1 * | 4/2008 | Evans ............. A61M 25/09041 604/164.13 |
| 2008/0154345 A1 * | 6/2008 | Taylor .................. A61B 1/3137 607/93 |
| 2009/0105654 A1 * | 4/2009 | Kurth .............. A61M 25/09041 604/170.03 |
| 2010/0081986 A1 * | 4/2010 | Matson ............... A61M 25/003 604/247 |
| 2014/0180089 A1 | 6/2014 | Alpert et al. |
| 2017/0303891 A1 * | 10/2017 | Yamashita ............... A61B 8/12 |
| 2019/0001103 A1 * | 1/2019 | Korkuch ........... A61M 25/0668 |

OTHER PUBLICATIONS

"Catheter." Merriam-Webster.com Dictionary, Merriam-Webster, https://www.merriam-webster.com/dictionary/catheter. Accessed May 2, 2023. (Year: 2023).*

* cited by examiner

MULTI-LUMEN INTRAVASCULAR CATHETERS WITH INNER CONVERGING LUMENS FOR MULTIPLE GUIDEWIRE CONTROL

RELATED APPLICATIONS

This application is a continuation-in-part of and claims the benefit of the Jul. 7, 2021 filing date of U.S. application Ser. No. 17/369,008, now abandoned, entitled "Multi-Lumen Intravascular Catheters with Inner Converging Lumens for Multiple Guidewire Control."

FIELD OF THE INVENTION

The present invention relates generally to apparatus for insertion of vascular catheters into blood vessels for the treatment of vascular disease, including multi-lumen catheters which are suitable for procedures using multiple guidewires of different diameters. More specifically, the present invention relates to multiple-lumen (sometimes called "multi-lumen") catheters in the treatment of vascular blockages, allowing rapid tracking and precise steering of the catheter and the guidewires therein while facilitating and enhancing the movement of catheter portions into particular blood vessels.

BACKGROUND OF THE INVENTION

A wide variety of percutaneous endovascular procedures exist in which a catheter or other miniature instrument is inserted percutaneously into a blood vessel to treat a vascular condition. Examples of commonly performed endovascular procedures to treat vascular blockages may include the insertion of a catheter and guidewire into a narrowed or occluded vessel so as to open an intravascular blockage with a balloon, a metallic stent, an atherectomy catheter, a laser catheter or any other treating device designed to open the blockage.

All vascular procedures begin with a vascular guidewire. Guidewires are the lead device when treating any narrowing or total blockage in the vascular system. In general, most endovascular treatment devices require safe passage of a guidewire across the lesion to provide support and over-the-wire tracking of the device through the target lesion. This fundamental step of traversing a lumen target with a guidewire may be challenging particularly when treating a chronic total occlusion (CTO) which is a particularly difficult vascular blockage.

Guidewires are produced in three common diameters, 0.014", 0.018" and 0.035", and may be classified by a variety of guidewire characteristics including but not limited to tip configuration and guidewire stiffness and diameter. There are presently in excess of one hundred guidewires available in today's market, all with different specifications and characteristics. As a guidewire exits the distal tip of a catheter to probe a vascular blockage, it is important that the guidewire tip retains its performance, i.e., moves precisely as the surgeon directs it to move. For instance, torque control and the ability to push a guidewire tip as desired by the surgeon may be lost in some applications, thereby reducing the ability to completely cross vascular lesions. There are a number of features of guidewires which are used to describe various aspects of guidewire performance. Among these are: steerability; trackability; torquability; support; flexibility; stiffness; tactile feedback; malleability; and radio-opacity and visibility. Such features are well-known to those skilled in the area of vascular surgery.

As guidewire technology evolves, operators continue to pursue the endovascular treatment of increasingly challenging vascular blockages. Guidewire support catheters have evolved as a complement to guidewires in assisting the operator to cross increasingly difficult anatomy.

There are a great number of single lumen and multi-lumen guidewire support catheters currently available. No known prior art catheter is specifically designed to fully support the guidewire to enable guidewire performance in controlling the direction of its distal tip, thereby maximizing its ability to completely negotiate difficult anatomy or to completely traverse blockages.

Typically, a single-lumen diagnostic catheter is tracked to the target lesion through a vascular sheath added for support. Once the catheter reaches a difficult vascular blockage, a guidewire of choice is passed through the catheter lumen and extended from its distal tip until it reaches the target to be treated. Probing of the lesion is initiated with the guidewire to penetrate the blockage while remaining in the true lumen of a blood vessel. The operator manipulates the guidewire and the support catheter into the blockage in an attempt to penetrate and cross (pass entirely through) the blockage. Because difficult vascular blockages are usually long, severely calcified lesions with a proximal fibrous cap, failure to pass the initial guidewire completely across the lesion is very common.

Furthermore, the guidewire may take an unwanted track into a subintimal space outside the true lumen or dissection plane, making it more difficult to get back to the proper track and reach the true lumen beyond the blockage. As a result, several guidewire exchanges may be necessary to successfully penetrate the entire length of the lesion, with each guidewire serving different functions. However, when a second guidewire is exchanged for and inserted within the blocked lumen, it is likely that it will follow the same path as the first guidewire. Because single-lumen catheters accommodate only one guidewire at a time, the necessary multiple guidewire exchanges are lengthy and labor-intensive. Because the distal tip of existing single-lumen catheters used to cross difficult vascular blockages is not typically designed to enhance its crossing profile or its steerability, repetitive passage of the different guidewires into the same path or subintimal space is common, with resultant unsuccessful re-entry into the reconstituted true lumen distal to the intravascular blockage. This strategy of wire escalation with a single-lumen support catheter is very common, and when unsuccessful, it can lead to longer procedures, increased radiation exposure, and increased complications including the need for amputation.

Within the prior art are numerous examples of multi-lumen catheters and guidewire-enabling catheters. For example, U.S. Pat. No. 5,292,305, issued on Mar. 8, 1994, discloses a double-lumen angioscopy catheter with separate passageways for a guidewire and an optic fiber bundle. The passageways are joined into a single tubular component for the distal portion of the catheter which enters the body. The guidewire can be used to maneuver the distal end of the optic fiber bundle to accomplish controlled inspection within a body vessel.

U.S. Pat. No. 6,290,668, issued on Sep. 18, 2001, discloses a catheter having a proximal shaft with two lumens and a distal shaft with a single lumen connected to the proximal shaft. A guidewire and a light guide are received in the first and second lumens respectively, of the proximal shaft, either of which may be extended into the single lumen of the distal shaft, the distal shaft being sufficiently flexible to facilitate movement of the catheter through tortuous paths. A hub is provided having ports through which appropriate fluids may be applied to the lumens.

U.S. Pat. No. 6,394,141, issued on May 28, 2002, discloses a catheter described as a single lumen to multiple lumen transition catheter. The single lumen is in fluid communication with each and every lumen comprising the multi-lumen portion.

U.S. Pat. No. 6,730,037, issued on May 4, 2004, shows a vascular catheter having a low-profile distal end which has a reduced cross-sectional area compared to that of the proximal region. The proximal region includes at least two lumens for accommodating a movable guidewire and a rotatable working element. The catheter body may be inserted over the movable guidewire, with the guidewire passing through a lumen in the distal region and the guidewire lumen in the proximal region. After positioning the catheter body, the guidewire can be retracted from the distal region and into the proximal region, leaving the lumen in the distal region available for the rotatable working element.

U.S. Pat. Nos. 8,162,891 and 8,801,691, issued on Apr. 24, 2012 and Aug. 12, 2014, disclose a support catheter for stowing and exchanging guidewires. A single contiguous lumen is formed from the proximal region through the distal region and has a larger proximal cross-sectional area than distal cross-sectional area.

Despite the several prior art attempts at multi-lumen catheters, no known prior art catheter allows a pair of guidewires first inserted through a proximal region of the catheter to be preloaded within the catheter concurrently while the different guidewires sequentially probe the target while retaining guidewire performance. Thus, a need exists for a dexterous catheter capable of use with multiple guidewires employed in treating various intravascular phenomena. In particular, a catheter configuration is needed that alleviates problems occasioned when a first guidewire has been directed outside of the vessel lumen or which cannot be advanced beyond a blockage. An improved catheter should increase the likelihood of a successful crossing of intravascular blockages. It would be highly advantageous to have a multiple-guidewire catheter system that avoids the above problems and solves the above-discussed limitations.

More importantly, by gentle retraction of one guidewire, the next preloaded guidewire can be quickly engaged to continue probing the blockage. The multi-lumen design offers rapid sequential probing of the blockage with two or more guidewires, therefore improving on procedural speed and accuracy.

OBJECTS OF THE INVENTION

A fundamental object of the present invention is to provide an improved catheter for better treating difficult vascular blockages.

It is also an object of this invention to provide a catheter that is configured such that multiple guidewires may be directed through lumens to arrive with improved precision at an intended target blockage.

Another basic object of the present invention is to provide a catheter which facilitates quick and accurate probing of difficult vascular blockages with two or more guidewires of different characteristics, and also to provide a catheter which facilitates sequential probing by preloaded guidewires with different characteristics.

Another object of this inventive catheter is to provide a catheter which allows alternating maneuvers between different guidewires through the distal catheter region to more effectively treat vascular blockages.

Another object of the present invention is to provide a catheter which is able to deliver fluid (e.g., contrast medium or a drug) while a guidewire remains in a beneficial position near the catheter tip.

Yet another object of this invention is to provide a catheter which reduces time-consuming guidewire exchanges during surgery.

An additional object of the present invention is to provide a catheter which results in excellent support, steerability, torquability and tactile feedback during vascular surgery.

These and other objects of the invention will be apparent from the following descriptions and from the drawings.

SUMMARY OF THE INVENTION

The present invention is an improved intravascular catheter for the interventional treatment of difficult vascular blockages. The invention is an improved multiple-lumen catheter having multiple guidewires for treatment of vascular blockages, the catheter comprising a proximal-end assembly, a distal-end portion and a multi-lumen medial portion therebetween. In the improvements, (1) the multiple guidewires are preloaded in the catheter, each guidewire in its own single-guidewire lumen extending from its own guidewire entry port in the proximal-end assembly to a lumen convergence portion; and (2) the distal-end portion includes (a) the lumen convergence portion along which the multiple lumens merge into a single output lumen sized to match the largest-diameter lumen of the multiple lumens, (b) an intermediate distal-end section connected to the lumen convergence portion and surrounding the single output lumen continuing therethrough, and (c) a tapered tip surrounding the single output lumen continuing therethrough.

In some highly-preferred embodiments, each lumen other than the single output lumen is sized to match the diameter of the guidewire passing therethrough.

In some highly-preferred embodiments, in the distal-end portion each lumen of the multiple lumens and the single-output lumen has its corresponding distal-end axis, and the distal-end axis of the single output lumen is substantially coincident with the distal-end axis of one of the multiple lumens when all of the distal-end axes are straight and mutually parallel.

In some highly-preferred embodiments of the inventive multi-lumen catheter, the proximal-end assembly includes (1) one lumen tube for each of the multiple lumens, each tube configured to receive one guidewire, and (2) a transition fixture configured to direct each of the guidewires from its corresponding lumen tube into one lumen of the multi-lumen medial portion. In some of these embodiments, the transition fixture includes a guidewire transition guide comprising (a) one guide tube for each of the multiple guidewires, each guide tube having a guide lumen with proximal and distal ends, the proximal end of each guide tube being aligned with its corresponding lumen tube and the distal end of each guide tube being aligned with its corresponding lumen in the multi-lumen medial portion, and (b) a transition guide web holding all of the guide tubes together. In some of these embodiments, each lumen other than the single output lumen is sized to match the diameter of the guidewire passing therethrough. In some of these embodiments, the guidewire transition guide may be an integrally-formed component, and such integrally-formed guidewire transition guides may be made of polymer material or may be metallic.

In some such preferred embodiments, each lumen tube receives its corresponding guidewire through a corresponding guidewire entry-port fitting attached to each lumen tube and defining its corresponding entry port.

In some highly-preferred embodiments of the inventive multi-lumen catheter, one or more of the multiple guidewires each has multiple physical characteristics, and the physical characteristics of all of the guidewires are not the same. In some of these embodiments, one or more of the multiple guidewires each has the physical characteristic of its diameter differing from the diameter of at least one other of the multiple guidewires, and in some of these embodiments, one or more of the multiple guidewires each has a differing stiffness from the stiffness of at least one other of the multiple guidewires.

In some preferred embodiments, the taper of the tapered tip reduces the tapered tip diameter to substantially the diameter of the single output lumen.

In some preferred embodiments, one of the multiple lumens, with its guidewire removed, is configured for fluid delivery to and through the tapered tip.

In some embodiments, each of the guidewires has a tip portion having a rest shape, and the rest shape of one or more of the guidewires is not substantially straight. In some embodiments, at least one of the multiple lumens in the distal-end portion of the inventive multi-lumen catheter is surrounded by an encircling reinforcement. Also in some embodiments, the distal-end portion of the inventive multi-lumen catheter includes at least one radio-opaque marker band.

In another aspect, the present invention is an improved multiple-lumen catheter configured to support multiple guidewires for treatment of vascular blockages. The catheter comprises a proximal-end assembly, a distal-end portion and a multi-lumen medial portion therebetween. The improvements are: (1) each of the multiple lumens is a single-guidewire lumen extending from its own guidewire entry port in the proximal-end assembly to a lumen convergence portion and (2) the distal-end portion includes (a) the lumen convergence portion along which the multiple lumens merge into a single output lumen sized to match the largest-diameter lumen of the multiple lumens, an intermediate distal-end section connected to the lumen convergence portion and surrounding the single output lumen continuing therethrough, and a tapered tip surrounding the single output lumen continuing therethrough.

The term "single-guidewire lumen" as used herein refers to a lumen which is configured to hold only a single guidewire, and may consist of a set of lumens arranged end-to-end.

The term "sized to match" as used herein with reference to lumen and guidewire diameters refers to a lumen diameter which permits the guidewire therein to move therealong while constraining lateral guidewire movement within the lumen such that the guidewire and the lumen remain substantially coaxial during use, thereby contributing to guidewire control and performance. In this definition, constraining lateral movement refers to such constraining being in all directions perpendicular to the local axis of the guidewire.

The term "rest shape" as used herein in describing the geometry of guidewire tips refers to the curvature of these tips when there are no external forces on the tips which may cause bending. The term rest shape is also used in describing the geometry of the distal-end portions of catheters.

The term "medical-grade" as used herein refers to materials which have been certified under an appropriate standard such as ISO:10993. Furthermore, parts or components which are of medical-grade have been manufactured in a facility which has been certified under an appropriate standard such as ISO 13485.

Note that the term "lumen" refers to a passageway in a structure such as a tube. In the field of the present invention, the term "lumen" may also be used in some instances to refer to passageways in bodily structures such as blood vessels, and these may be referred to as true lumens.

BRIEF DESCRIPTION OF THE DRAWINGS

FIGS. 9A-9C are longitudinal sectional views of three alternative embodiments of the distal-end portion of the inventive catheter described herein.

FIGS. 10A-10J are sequential sectional and schematic views of the distal-end portion of FIG. 9B, illustrating the use of the inventive catheter in a procedure involving the sequential engagement of two preloaded guidewires with a CTO.

FIGS. 11A-11C are sectional and schematic views which illustrate in exaggerated fashion the operation of a catheter having the distal-end portion of FIG. 9B, showing how a second guidewire can probe the blockage in a slightly different space than the first guidewire because of the angular orientation of the catheter tip.

DETAILED DESCRIPTION OF PREFERRED EMBODIMENTS

FIGS. 1-7D are a set of figures which illustrate an embodiment 30 of the inventive multi-lumen catheter (also referred to herein as catheter 30). Catheter 30 includes two preloaded guidewires 88 and 90 (see FIGS. 10A-11C). Guidewires 88 and 90 may have different diameters and other physical characteristics such as tip shape. Catheter 30 is both a crossing catheter and a support catheter and is intended to be used in over-the-wire mode. Note that the number of guidewires in catheter 30 is not intended to be limiting; the inventive catheter may be configured to use more than two guidewires. Also note that for simplicity throughout this detailed description, not every instance of an element in a figure is labeled with a reference number; in these instances, the context of the figures is nevertheless clear.

Figure 1:
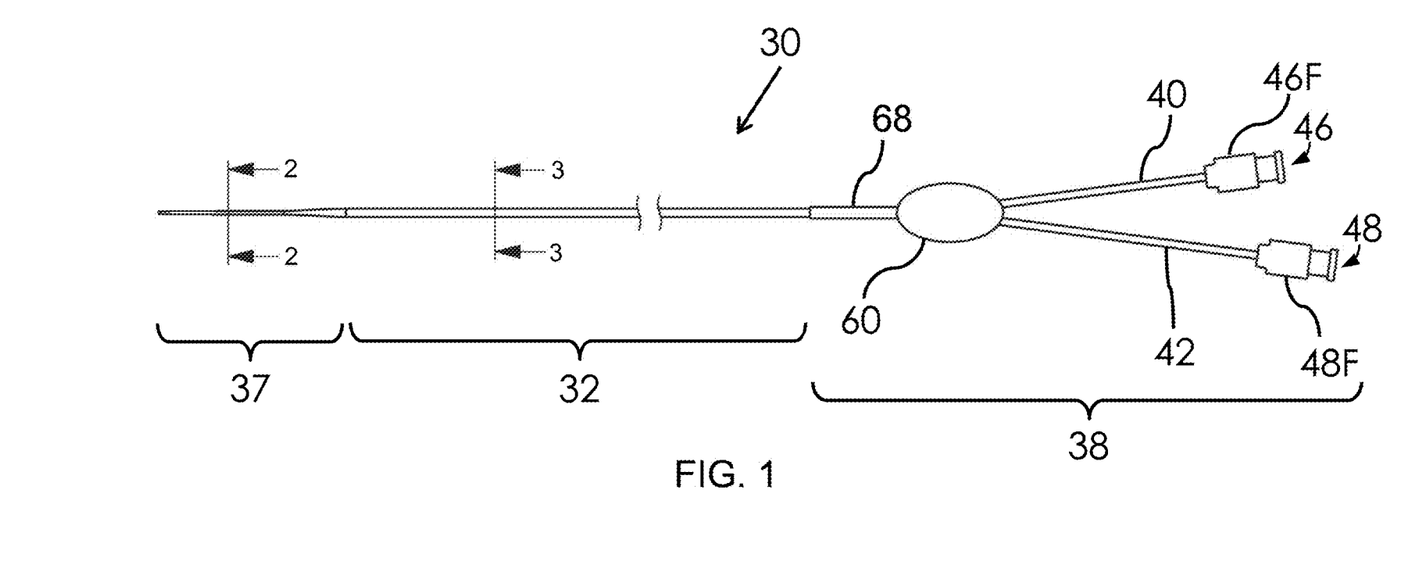
FIG. 1 is a side-elevational view of an embodiment of the multi-lumen catheter of this invention.
Figure 3:
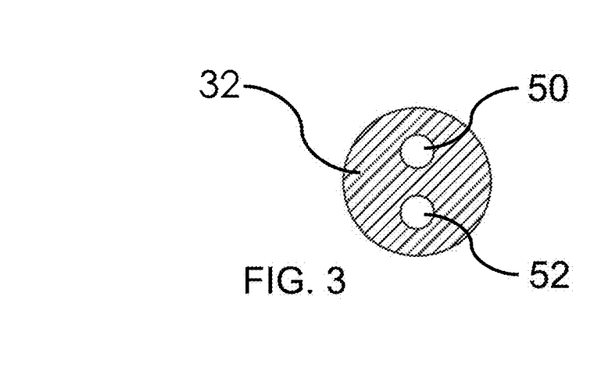
FIG. 3 is an enlarged cross-sectional view of the multi-lumen medial portion of the catheter embodiment of FIG. 1, taken along line 3-3 as indicated in FIG. 1.
Figure 4:
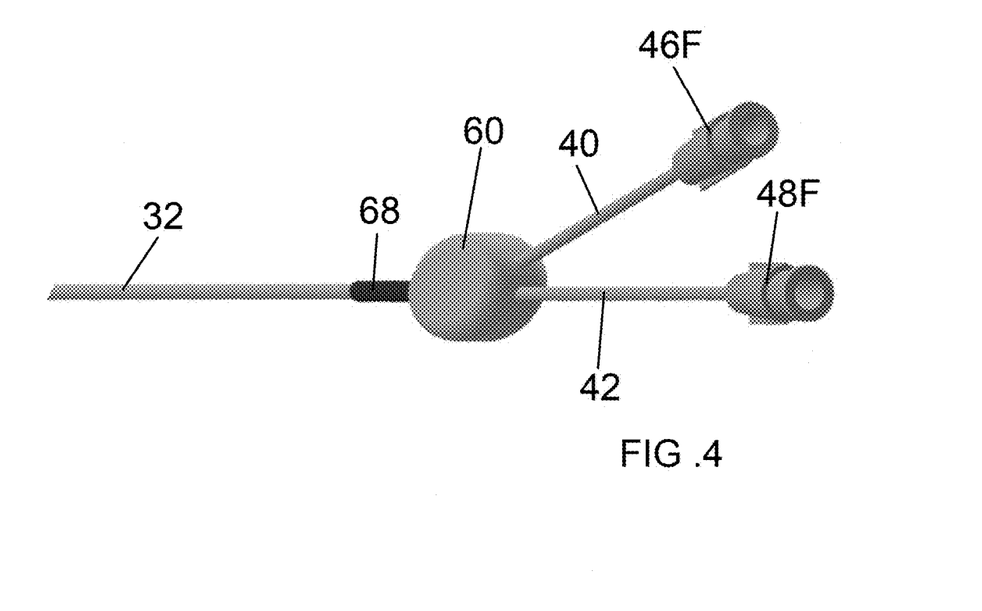
FIG. 4 is a truncated perspective-view illustration of the embodiment of the multi-lumen catheter of FIG. 1. The catheter has been truncated at a point along the multi-lumen medial portion near the proximal-end assembly of the catheter.
Figure 5:
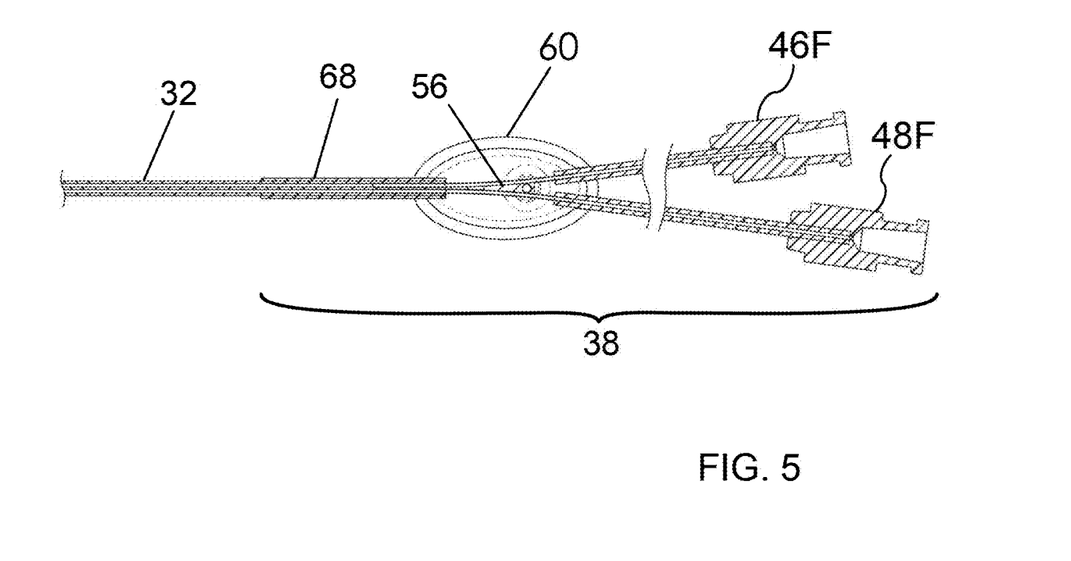
FIG. 5 is a side-elevation sectional view of the truncated catheter of FIG. 4, taken along the longitudinal central bisecting plane of the catheter.

Referring primarily to FIGS. 1, 4 and 5, in addition to guidewires 88 and 90, catheter 30 includes a proximal-end assembly 38, a multi-lumen medial portion 32, and a distal-end portion 37. Many of the elements of catheter 30 may be made of medical-grade elastomer or thermoplastic known in the art. Preferably, the major tubular portions of catheter 30 are made of extruded thermoplastic polymer tubing. Multi-lumen medial portion 32 is an elongated tube having two parallel lumens 50 and 52 (see FIG. 3) each surrounding its corresponding guidewire 88 and 90, respectively.

Proximal-end assembly 38 includes two input fittings 46F and 48F which define guidewire entry ports 46 and 48, respectively, and which receive guidewires 88 and 90, respectively. Fittings 46F and 48F may, for example, be Luer fittings and are connected to two lumen tubes 40 and 42, respectively, to enable connection of a syringe for pretreatment flushing. Lumen tubes 40 and 42 are connected to a transition fixture 60 which guides guidewires 88 and 90 from individual lumen tubes 40 and 42 into multi-lumen medial portion 32 of catheter 30.

Figure 8A:
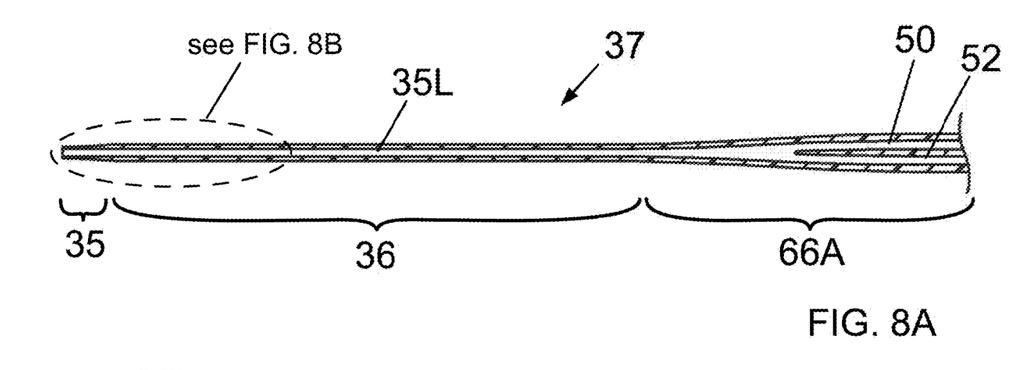
FIG. 8A is an enlarged sectional view of the distal-end portion of the catheter embodiment of FIG. 1.
Figure 8B:
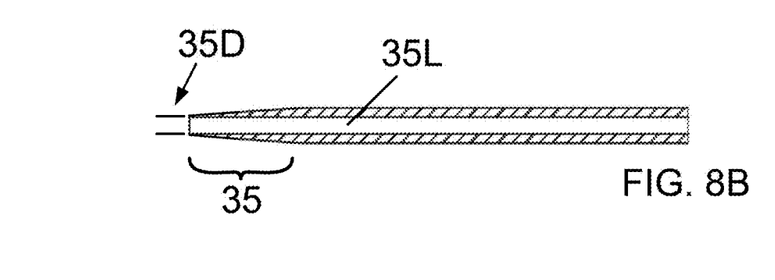
FIG. 8B is a further enlarged sectional view of the distal-end portion shown in FIG. 8A, particularly illustrating the tapered tip of the distal-end portion and the single output lumen therein.

Referring to FIGS. 8A and 8B (see also FIGS. 2 and 3), distal-end portion 37 includes a lumen convergence region 66A in which lumens 50 and 52 merge into a single output lumen 35L, an intermediate distal-end section 36 surrounding single-output lumen 35L, and a tapered tip 35 which, along with a guidewire extending therethrough, engages vascular blockages during use of the catheter 30. Single output lumen 35L is sized to match the largest-diameter lumen of multiple lumens 50 and 52.

One of the main performance features of tapered tip 35 is to penetrate a vascular blockage by being able to track along a guidewire into a vascular blockage in an unobstructed fashion. (See FIGS. 10A-10J and their related description.) The taper of tapered tip 35 may take a variety of shapes which allow such tracking, and the specific shape of tapered tip 35 as shown in the figures of this application is not intended to be limiting. In particular, the length along which the taper exists may vary substantially, from a steep shorter taper to a gentle longer taper, and the taper may not be a linear taper but may be curved, or even simply rounded at the end.

During a procedure, a particular kind of obstruction, which in the field of vascular surgery is known as "lipping," can occur when the cross-sectional area of single output lumen 35L of tapered tip 35 is larger than the guidewire therein. In some highly-preferred embodiments of catheter 30, tapered tip 35 may be tapered down substantially to a diameter 35D of single output lumen 35L, as illustrated in FIG. 8B, in order to minimize the effect of lipping.

Figure 8C:
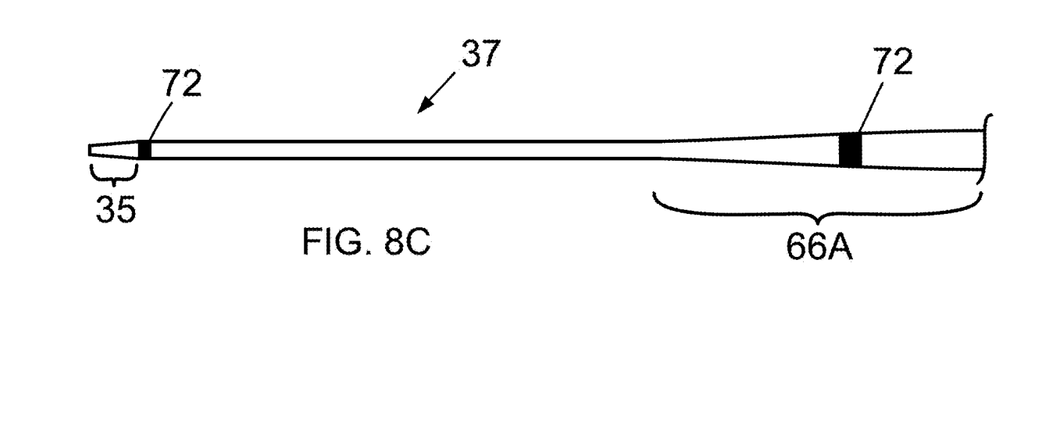
FIG. 8C is a side elevation of an embodiment of the distal-end portion of the inventive catheter disclosed herein, illustrating the inclusion of two radio-opaque marker bands on the distal-end portion.

FIG. 8C illustrates an embodiment in which distal-end portion 37 of catheter 30 includes two radio-opaque marker bands 72, one such marker band adjacent to tapered tip 35 and the other within convergence region 66B. Marker bands 72 are present to enable the location of distal-end portion 37 to be visible fluoroscopically as well as to provide markers from which measurements may be made during a surgical procedure.

Figure 6:
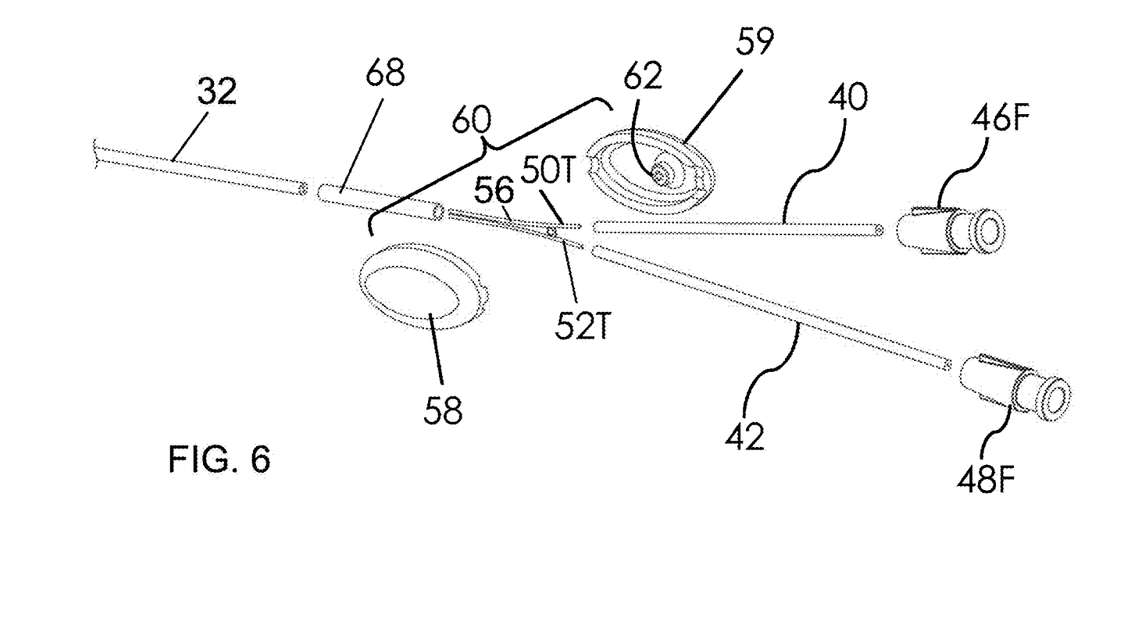
FIG. 6 is a partially exploded isometric view of the truncated catheter of FIG. 4, particularly detailing an embodiment of the transition fixture.
Figure 7A:
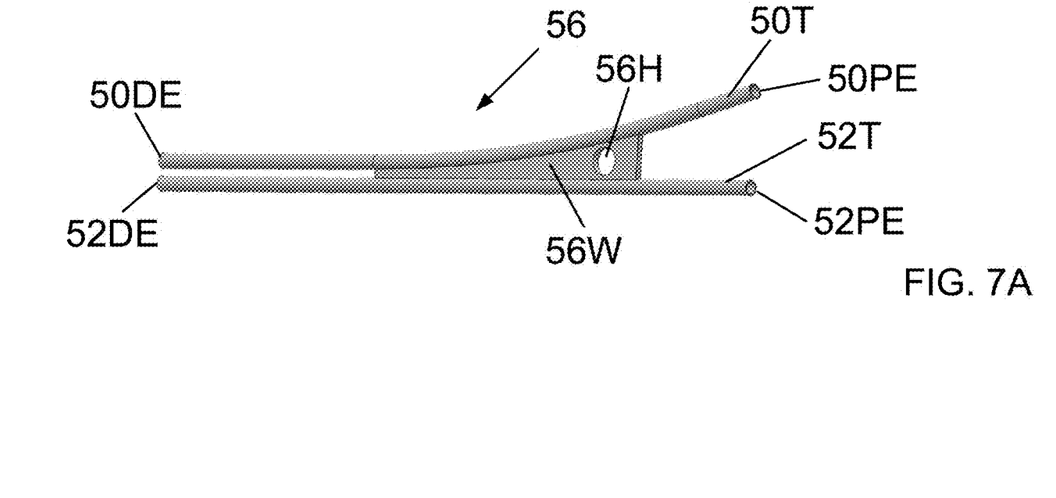
FIG. 7A is an enlarged and perspective-view illustration of the guidewire transition guide shown in FIG. 6.
Figure 7B:
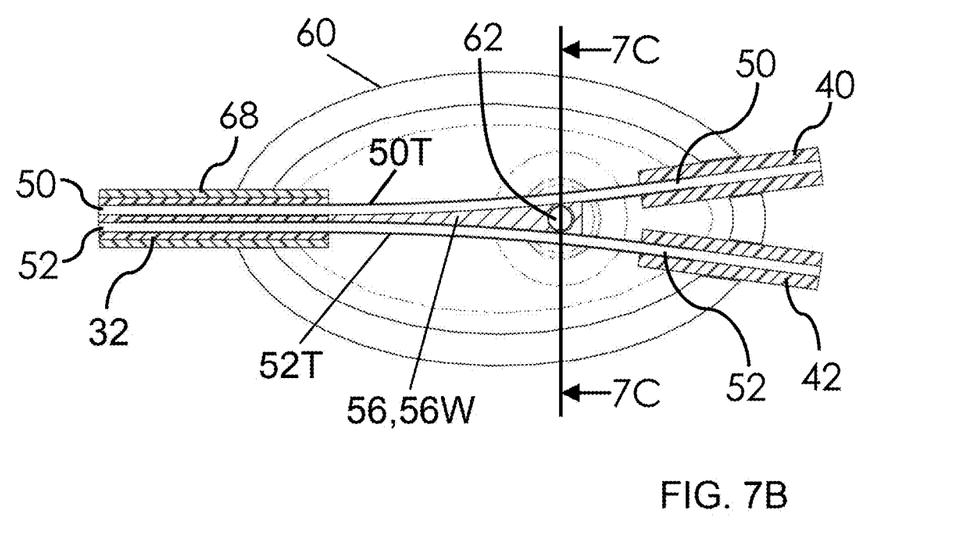
FIG. 7B is an enlarged sectional view detailing the transition fixture and the proximal-end assembly and multi-lumen medial portion connections thereto.
Figure 7C:
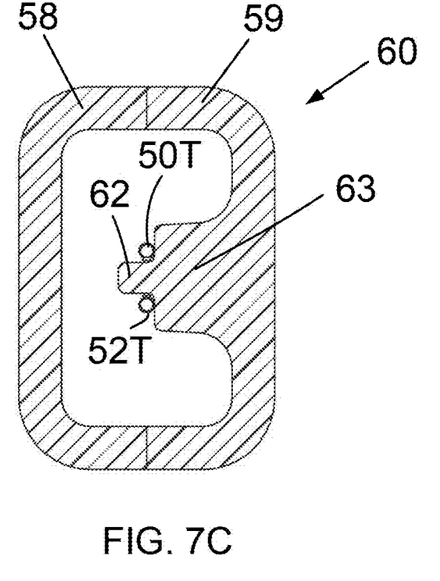
FIG. 7C is an enlarged cross-sectional view of the transition fixture taken along line 7C-7C as indicated in FIG. 7B.

Referring to FIGS. 6-7A, transition fixture 60 includes a guidewire transition guide 56 which includes two guide tubes 50T and 52T which surround lumens 50 and 52, respectively, and a transition guide web 56W which holds guide tubes 50T and 52T together. Guide tubes 50T and 52T each have guide-tube proximal ends 50PE and 52PE and guide-tube distal ends 50DE and 52DE, respectively. Guide-tube proximal ends 50PE and 52PE are aligned with their corresponding lumen tubes 40 and 42, respectively, and guide-tube distal ends 50DE and 52DE are aligned with their corresponding lumens 50 and 52 of multi-lumen medial portion 32, respectively.

Catheter 30 includes internal guidewire-receiving (also referred to herein as guidewire-surrounding) lumens 50 and 52 as passageways which extend through catheter 30 from guidewire entry ports 46 and 48, respectively, passing through other elements of proximal-end assembly 38 and multi-lumen medial portion 32 to lumen convergence region 66A of distal-end portion 37. Lumens 50 and 52 are single-guidewire lumens each extending from its own guidewire entry port 46 and 48, respectively, in proximal-end assembly 38 to lumen convergence portion 66A. In embodiment 30, lumens 50 and 52 are each sized to match their corresponding guidewires 88 and 90, respectively, such that guidewires 88 and 90 are able to move longitudinally along lumens 50 and 52, respectively, while being laterally-constrained within their respective lumens 50 and 52. Such sizing of lumens 50 and 52 along their entire length provides excellent control of guidewire movement which enables the surgeon to achieve that which is necessary for beneficial engagement of vascular blockages. In general, guidewires may vary in size and function and may have different characteristics such as caliber, weight, stiffness, steerability, torquability and trackability. Thus, the dimensions and other physical characteristics of catheter 30 may vary such that lumens 50 and 52 accommodate guidewires 88 and 90 in a fashion which enables the performance of guidewires 88 and 90 and catheter 30 to meet a set of desired performance features.

Figure 7D:
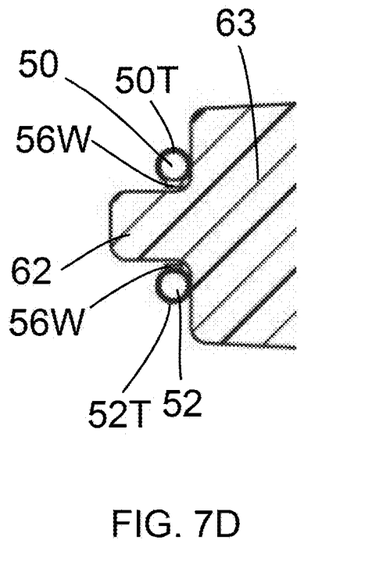
FIG. 7D is a further enlargement of a portion of FIG. 7C to illustrate in detail the guidewire transition guide in the cross-section of the transition fixture.

Referring now to FIGS. 6-7D, transition fixture 60 includes a pair of fixture body segments 58 and 59. Fixture body segments 58 and 59 are preferably injection-molded elements bonded together during assembly. Fixture body segment 59 includes an inner salient 63 projecting towards the interior of fixture 60, and inner salient 63 includes a guide mount 62 on which guidewire transition guide 56 is mounted via a mounting hole 56H formed in transition guide web 56W. As noted above, guidewire transition guide 56 includes guide tubes 50T and 52T through which guidewires 88 and 90, respectively, are guided in lumens 50 and 52 from lumen tubes 40 and 42. As lumen tubes 40 and 42 connect to transition fixture 60, tubes 40 and 42 are oriented relative to each other at an acute angle, and as lumens 50 and 52 extend through lumen tubes 50T and 52T respectively, lumens 50 and 52 are gently reoriented into parallel passageways within multi-lumen medial portion 32. FIGS. 7C and 7D are cross-sectional illustrations of portions of transition fixture 60 taken along line 7C-7C of FIG. 7B which provide further clarifying detail of the configuration of transition fixture 60. In particular, note in the further-enlarged cross-sectional view of FIG. 7D the small portions of transition guide web 56W between guide tubes 50T,52T and guide mount 62.

Proximal-end assembly 38 also includes a stabilizer 68 (see FIGS. 1, 4, 5, 6 and 7B) which provides a stable mechanical connection between guidewire transition guide 56 of transition fixture 60 and multi-lumen medial portion 32. Stabilizer 68 concentrically surrounds multi-lumen medial portion 32, thereby strengthening the section of multi-lumen medial portion 32 adjacent to transition fixture 60. Stabilizer 68 is preferably made of thermoplastic polymer tubing.

Figure 2:
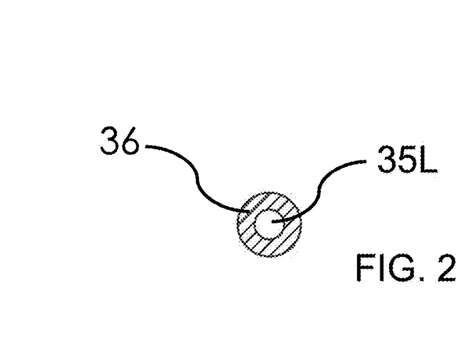
FIG. 2 is an enlarged cross-sectional view of the intermediate distal-end section of the catheter embodiment of FIG. 1, taken along line 2-2 as indicated in FIG. 1.
Figure 9A:
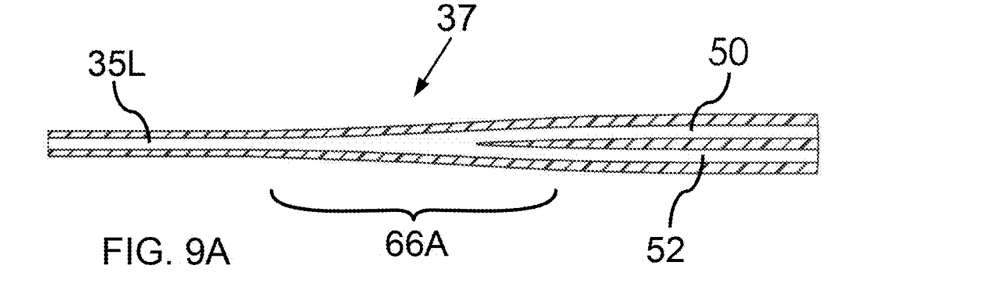
FIG. 9A illustrates an embodiment in which the axes of neither of the lumens of the multi-lumen medial portion are coincident with the axis of the single output lumen of the catheter.

FIGS. 9A-9D illustrate further detail of embodiments of distal-end portion 37 of inventive catheter 30. Note that all illustrations of distal-end portions in FIGS. 9A-9C do not include tapered tip 35. FIG. 9A depicts an embodiment (also indicated by reference number 37) in which neither a distal-end axis 50X of lumen 50 nor a distal-end axis 52X of lumen 52 (both lumens being lumens of multi-lumen portion 32) is coincident with a distal-end axis 35X of single output lumen 35L when all such axes 50X, 52X and 35X are straight and mutually parallel. (See FIGS. 11A and 11C for the relevant reference numbers and visualization of these axis definitions.) As mentioned above, distal-end portion 37 includes lumen convergence region 66A, and prior to (to the right of) region 66A, the cross-section of distal-end portion 37 is as shown in FIG. 3 and after (to the left of) region 66A, the cross-section of distal-end portion 37 is as shown in FIG. 2.

Figure 9B:
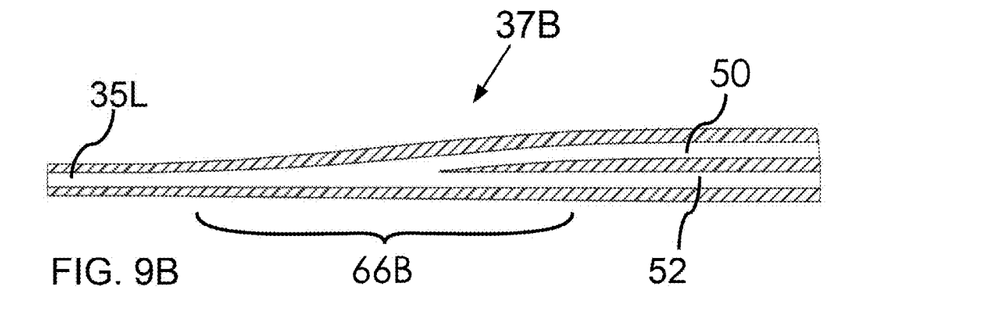
FIG. 9B illustrates another embodiment in which the axis of one of the lumens of the multi-lumen medial portion is coincident with the axis of the single output lumen of the catheter.

FIG. 9B illustrates an alternative distal-end-portion embodiment 37B in which axis 52X of lumen 52 is substantially coincident with axis 35X of single output lumen 35L. (As above, see FIGS. 11A and 11C for axis definitions.) Distal-end portion 37B includes lumen convergence region 66B, and prior to region 66B (i.e., to the right thereof), the cross-section of distal-end portion 37B is as shown in FIG. 3 and after region 66B (i.e., to the left of), the cross-section of distal-end portion 37B is as shown in FIG. 2. The geometry of lumen convergence region 66B has lumen 50 entering lumen convergence region 66B at an angle with respect to single output lumen 35L. Thus guidewires 88 and 90 are more precisely controlled by such structure of distal-end portion 35. See FIGS. 11B and 11C and their descriptions for further detail regarding lumen convergence region 66B. The characteristics of guidewire 88 such as stiffness may be transmitted to lumen 35L with resulting beneficial deflection.

Figure 9C:
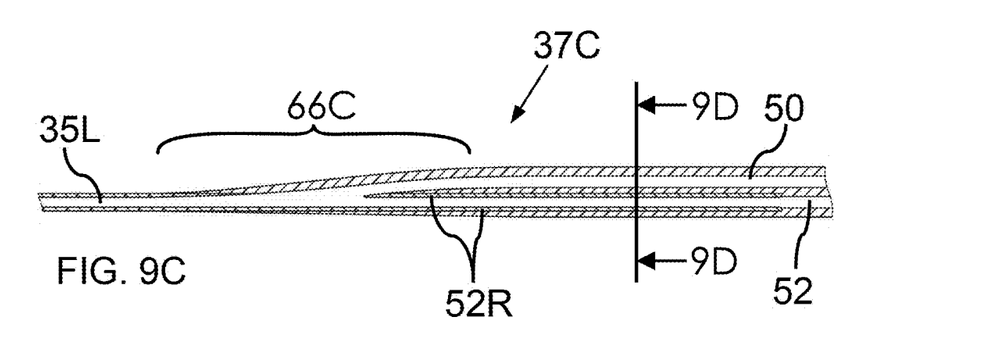
FIG. 9C illustrates yet another embodiment in which the axis of one of the lumens of the multi-lumen medial portion is coincident with the axis of the single output lumen of the catheter, and such coincident lumen is surrounded with multi-layered material to change the physical characteristics of the material surrounding such lumen.
Figure 9D:
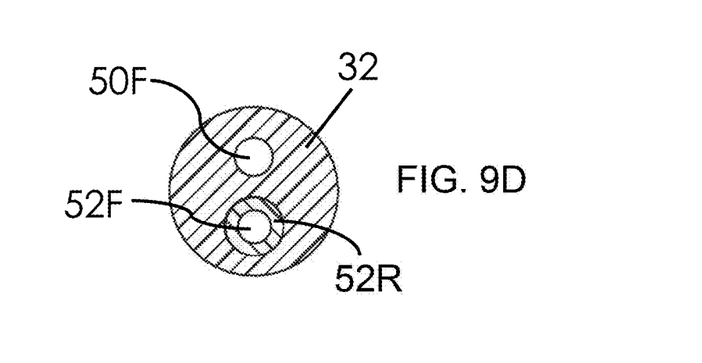
FIG. 9D is an enlarged cross-sectional view taken along line 9D-9D of the embodiment of the distal-end portion as indicated in FIG. 9C.

FIG. 9C illustrates another alternative distal-end-portion embodiment 37C. The geometry of embodiment 37C is similar to that of embodiment 37B, but embodiment 37C includes a lumen convergence region 66C with an encircling reinforcement 52R within lumen 52 as multi-lumen medial portion 32 enters a lumen convergence region 66C. Reinforcement 52R forms a multi-layered section with the material of multi-lumen medial portion 32 and distal-end portion 37C to change the physical characteristics (e.g., resilience) of the material surrounding lumen 52. FIG. 9D is an enlarged cross-sectional view taken along line 9D-9D of the embodiment of the distal-end portion of FIG. 9C. Such changes of material characteristics assist in the process of controlling guidewire movement during vascular surgical procedures.

FIGS. 10A-10J are sequential sectional and schematic views of distal-end portion 66B of FIG. 9B, illustrating with a simplified example the use of catheter 30 in a surgical procedure involving the sequential engagement of preloaded guidewires 88 and 90 with a chronic total occlusion 84 (hereinafter CTO 84) in an interior 87 of an obstructed blood vessel 82. In the surgical procedure, CTO 84 is to be engaged by probing with guidewires 88 and 90 during surgery.

Figures 10A, 10B, 10C:
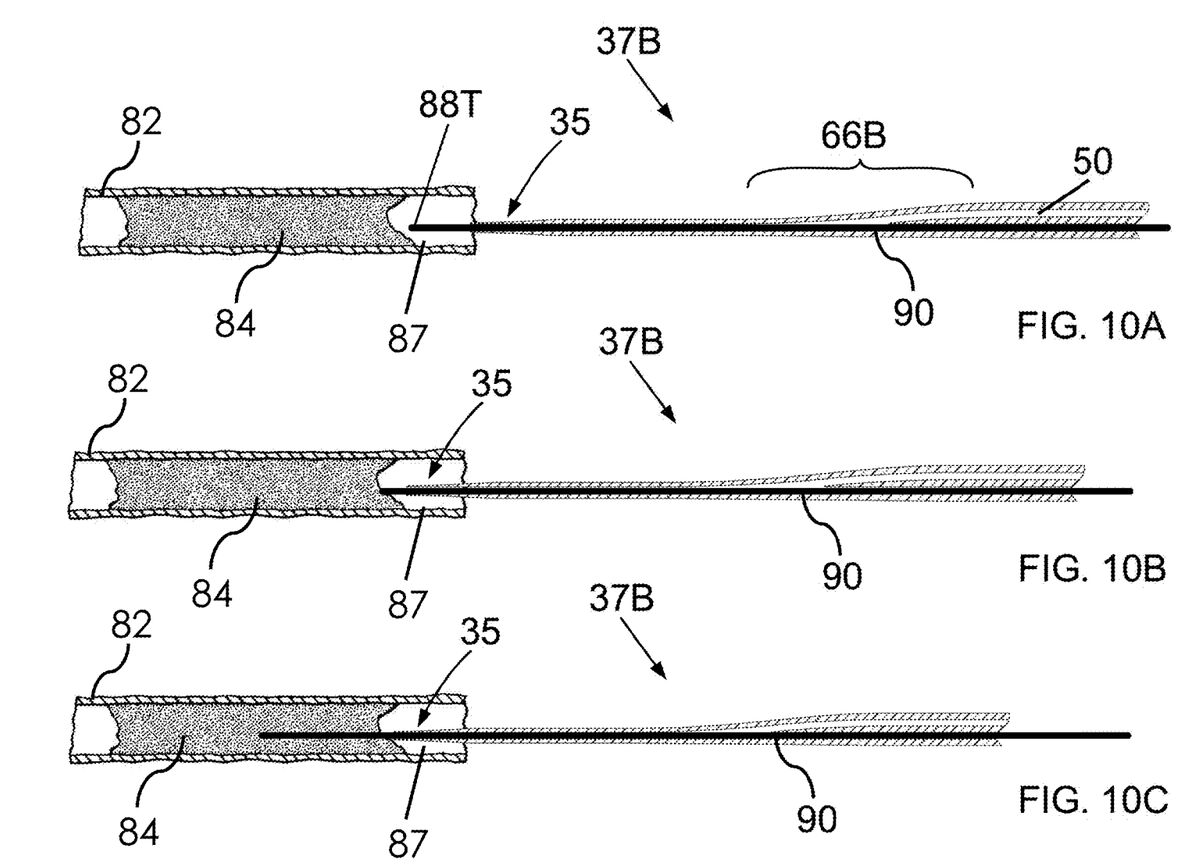
FIG. 10A illustrates a first guidewire extending from the tapered tip and in a position to interact with a CTO in a blood vessel.
FIG. 10B illustrates the first guidewire at a point of engagement with the CTO.
FIG. 10C illustrates the first guidewire having penetrated into the CTO, and the tapered tip of the distal-end portion of the catheter at a point of penetration into the CTO.

FIG. 10A illustrates guidewire 90 extending from tapered tip 35 (hereinafter tip 35) and in a position to interact with CTO 84. FIG. 10B illustrates guidewire 90 at a point of engagement with CTO 84, and FIG. 10C illustrates guidewire 90 having penetrated into CTO 84 as far as it may be advanced with tip 35 of distal-end portion 37B of catheter 30 at a point of penetration into CTO 84.

Figure 10D:
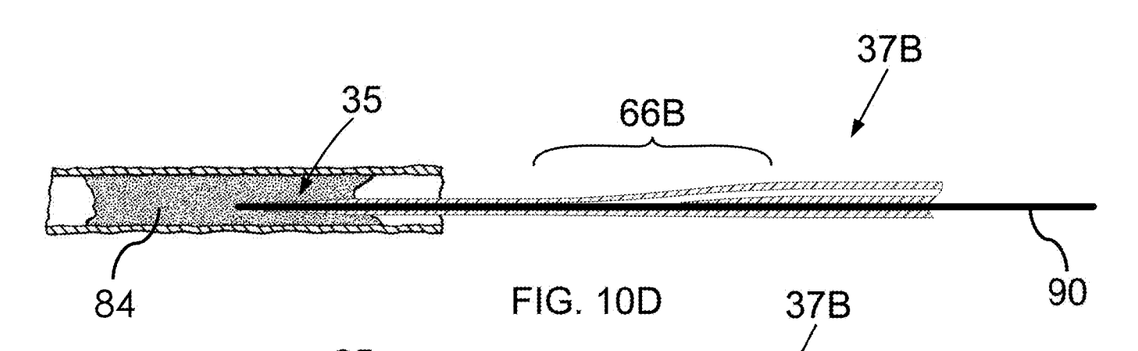
FIG. 10D illustrates the tapered tip advanced into the CTO along the first guidewire.
Figure 10E:
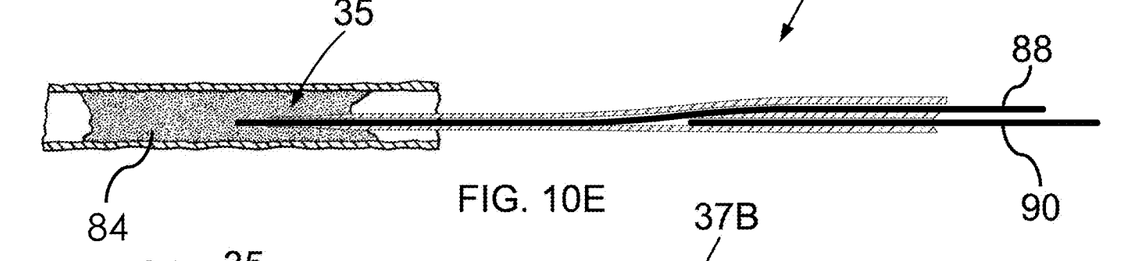
FIG. 10E illustrates the first guidewire withdrawn past the lumen convergence region of the distal-end portion and the second guidewire inserted into the CTO. The second guidewire has been inserted, while generally along the same path as the first guidewire, actually beneficially slightly off-path by virtue of catheter tip deflection. (See FIG. 11C for exaggerated illustration of such catheter-tip deflection.)

As the procedure continues, FIG. 10D illustrates tip 35 having advanced into CTO 84 along the path of guidewire 90. Next, FIG. 10E illustrates guidewire 90 having been withdrawn past lumen convergence region 66B of distal-end portion 37B and guidewire 88 advanced into CTO 84. Guidewire 88 has been inserted, while generally along the same path as guidewire 90, along a path slightly offset from that of guidewire 90 by virtue of the beneficial deflection of tip 35. See FIG. 11C for exaggerated illustration of such catheter-tip deflection. It should be noted that the paths of guidewires 88 and 90 may also be the same for certain sequential steps in a surgical procedure, for example if the surgeon wishes to insert the other guidewire along such a path to take advantage of the different physical characteristics of the other guidewire.

Figure 10F:
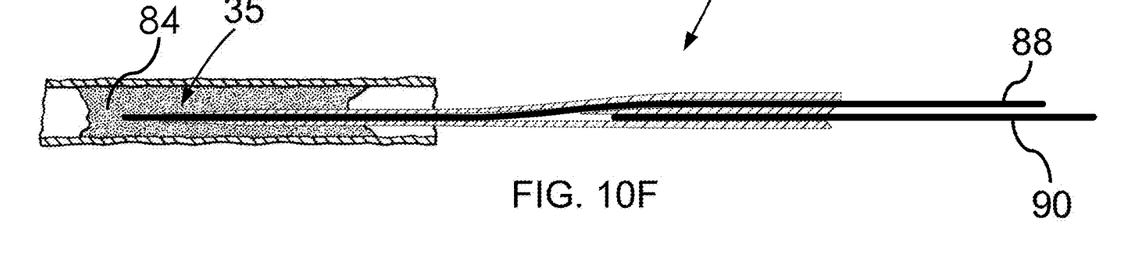
FIG. 10F illustrates the second guidewire having been advanced further into the CTO with the tapered tip tracking therealong.
Figures 10G, 10H, 10J:
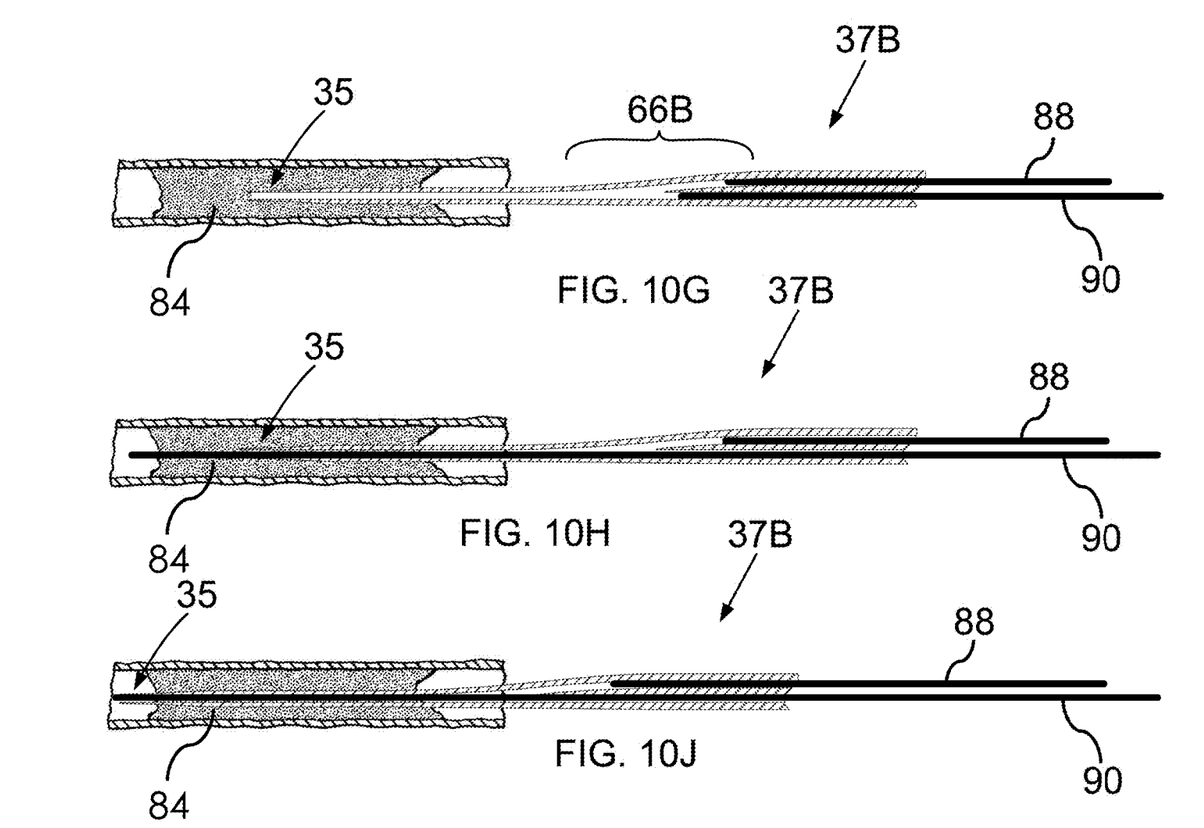
FIG. 10G illustrates both guidewires withdrawn from the CTO.
FIG. 10H illustrates the first guidewire again inserted into and subsequently having crossed the CTO.
FIG. 10J illustrates both the second guidewire and the tapered tip of the catheter having crossed the CTO.

Next, FIG. 10F illustrates guidewire 88 having been advanced farther into CTO 84 as far as it may be with tip 35 advanced therealong; FIG. 10G illustrates guidewires 88 and 90 both withdrawn from CTO 84; FIG. 10H illustrates guidewire 90 again inserted into and subsequently having crossed CTO 84; and FIG. 10J illustrates both guidewire 90 and tip 35 of catheter 30 having crossed CTO 84.

Figure 11A:
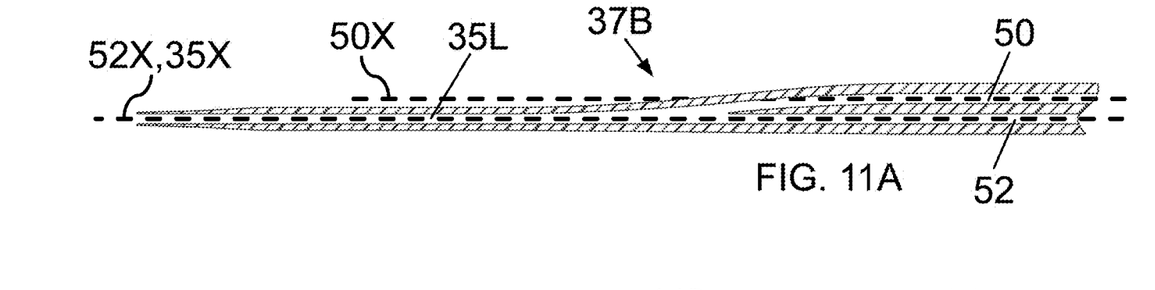
FIG. 11A illustrates the distal-end portion of FIG. 9B with definitions of the axes of various lumens.
Figure 11B:
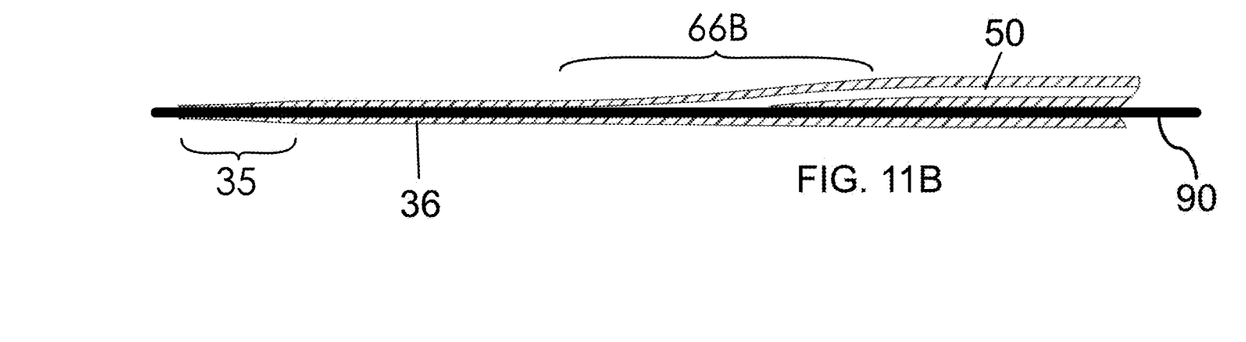
FIG. 11B illustrates the distal-end portion of FIG. 11A with a first guidewire extending through the tapered tip of the distal-end portion.
Figure 11C:
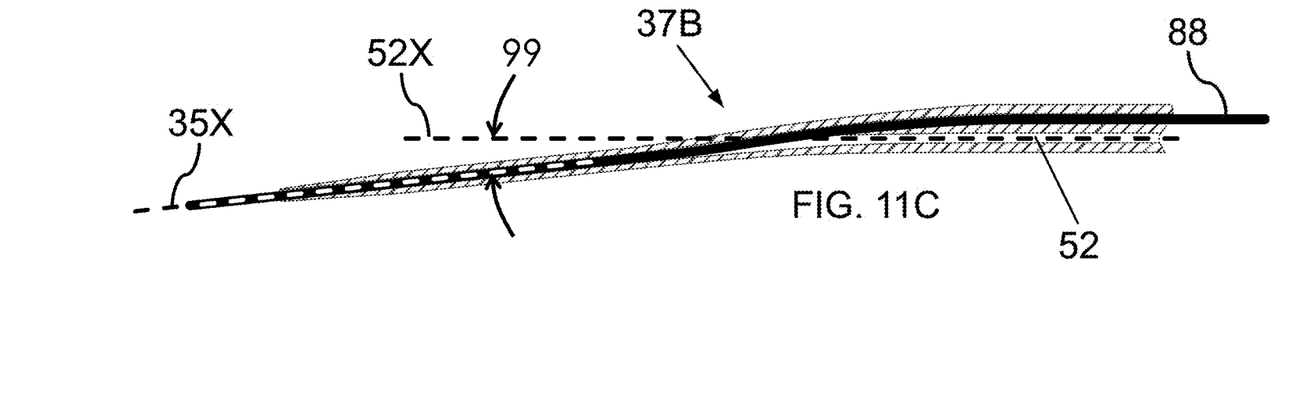
FIG. 11C illustrates the distal-end portion of FIG. 11A with the first guidewire withdrawn and a second guidewire extending through the tapered tip which is oriented at an acute angle to the lumen of the first guidewire.

FIGS. 11A-11C are sectional and schematic views which illustrate in exaggerated fashion the operation of catheter 30 having distal-end portion 37B. These figures show how guidewire 88 may be directed through tip 35 at an acute angle 99 relative to guidewire 90. Such manipulable angular orientation of distal-end portion 37B of catheter 30 provides a surgeon more options in how to engage vascular blockages during such critical procedures. As stated above, FIG. 11A provides a marked-up distal-end portion 37B for the purpose of defining the various axes needed for the following description.

FIG. 11B illustrates distal-end portion 37B having guidewire 90 extending through tip 35 with lumens 50, 52 and 35L mutually parallel, and FIG. 11C illustrates (a) distal-end portion 37B with guidewire 90 withdrawn, (b) guidewire 88 extending through tip 35, and (c) tip 35 oriented at acute angle 99 relative to lumen 52 with guidewire 90 withdrawn.

With guidewire 88 engaged as in FIGS. 10E and 10F, subsequent manipulation of guidewire 88 by the surgeon may more precisely negotiate CTO 84. For example, if guidewire 88 is stiffer than guidewire 90, distal-end portion 37B allows torque transmission to tip 35 via a stiffer guidewire 88.

As guidewire 90 progressively engages CTO 84, tip 35 will follow into CTO 84 as illustrated in FIGS. 10D and 10F. Tip 35 is tapered down to diameter 35D with very close to or substantially the same diameter as that of lumen 35L which is size-matched to the diameter of guidewire 88 or 90, whichever is larger. This enables portions of tip 35 to smoothly enter CTO 84 as guidewire 90 forcibly traverses CTO 84. Furthermore, after tip 35 enters CTO 84, it will remain in CTO 84 after withdrawal of guidewire 90. With tip 35 plunged into CTO 84 as shown in FIG. 10D, control of guidewire 88 is enhanced. Thus, when guidewire 88 is thereafter inserted (FIGS. 10E and 10F), guidewire 88 will exit tip 35 into CTO 84 in a region slightly spaced away from the region previously engaged by now-withdrawn guidewire 90 due to deflection of tip 35.

Importantly, guidewire 90 may be retracted somewhat and withdrawn, to the position illustrated in FIG. 10E. With guidewire 90 withdrawn to such a non-interference position, guidewire 88 may be deployed as in FIGS. 10E and 10F without completely removing guidewire 90 from catheter 30. Further, since tip 35 had been embedded within CTO 84 as tip 35 followed guidewire 90, guidewire 88 will emerge from tip 35 in a slightly different region than originally targeted in CTO 84 during initial penetration by guidewire 90.

As mentioned, partial withdrawal of guidewire 90 provides clearance for guidewire 88. Once guidewire 88 has been partially extracted (FIG. 10G), guidewire 90 may once again penetrate CTO 84, exiting tip 35 well within CTO 84 (FIG. 10H). Guidewire 90 and tip 35 may eventually clear CTO 84 as in FIG. 10J. Penetration of CTO 84 may also reoccur by guidewire 88, which may be of a larger diameter and/or stiffer than guidewire 90 as well as differing in other physical characteristics. FIGS. 10H and 10J illustrate how alternating use and switching between guidewires is facilitated.

Figure 12:
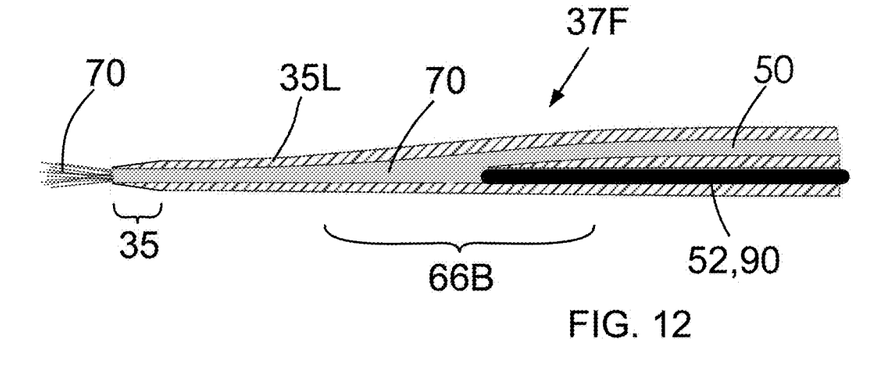
FIG. 12 illustrates in cross-section a distal-end portion which is configured to deliver a fluid such as contrast medium or medication through the tapered tip of the inventive catheter.

Catheter 30 is configured to be able to deliver fluids which the surgeon desires to inject into vessel 82 (see FIG. 12) during a procedure. FIG. 12 illustrates distal-end portion 37F which is configured to deliver a fluid 70 such as contrast medium or medication through tapered tip 35. In such configuration, guidewire 88 (not shown) is withdrawn from catheter 30 and fitting 46F on lumen tube 40 (see for example, FIG. 4) is configured to receive fluid 70 into guidewire entry port 46 (see FIGS. 10A-10J). Advantageously, guidewire 90 remains in lumen 52 of distal-end portion 37F to provide some control of penetrating tip 35 positioning.

Figure 13:
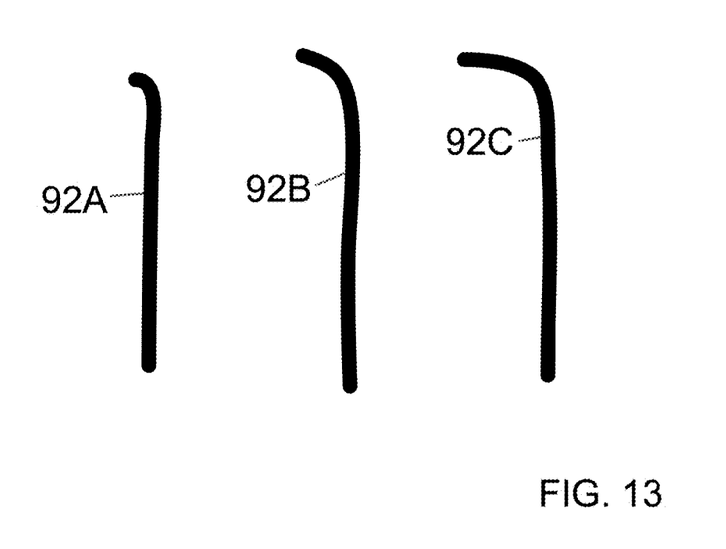
FIG. 13 illustrates three guidewire tip portions which have rest shapes that are not straight.

Catheter 30 is able to accommodate guidewires which are not merely straight but have geometry which in an unloaded state (under no external forces) may have a variety of shapes which provide various performance options for the surgeon. FIG. 13 illustrates three exemplary guidewire tip portions 92A, 92B and 92C which have rest shapes which are curved in a beneficial manner. Guidewire tip portions 92A, 92B and 92C are not intended to be limiting; catheter 30 is configured to accommodate a wide variety of guidewire shapes and guidewire tip shapes. In similar fashion, distal-end portion 37 of catheter 30 may also be configured to have geometry in which the shape of distal-end portion 37 is not straight. The shapes and other physical characteristics of guidewires 88 and 90 and distal-end portion 37 of catheter 30 cooperate during a surgical procedure, resulting in a wide variety of options for geometry and performance for the surgeon.

While the principles of this invention have been described in connection with specific embodiments, it should be understood clearly that these descriptions are made only by way of example and are not intended to limit the scope of the invention.

The invention claimed is:

1. In a multiple-lumen catheter having multiple guidewires for treatment of vascular blockages, each of the multiple lumens being circular in cross-section and having a diameter, the catheter comprising a proximal-end assembly and an elongate tube including a multi-lumen medial portion and a distal-end portion therebeyond, the improvement wherein:

the multiple guidewires are preloaded in the catheter, each guidewire in its own single-guidewire lumen extending from its own guidewire entry port in the proximal-end assembly through the medial portion of the elongate tube to a lumen convergence portion of the elongate tube;

the distal-end portion of the elongate tube includes (a) the lumen convergence portion along which the multiple lumens merge into a single output lumen being sized to match the largest-diameter lumen of the multiple lumens, (b) an intermediate distal-end section extending from the lumen convergence portion and surrounding the single output lumen continuing therethrough, and (c) a tapered tip at the end thereof and surrounding the single output lumen continuing therethrough;

the proximal-end assembly includes (d) one lumen tube for each of the multiple lumens, each tube configured to receive one guidewire, and (e) a transition fixture configured to direct each of the guidewires from its corresponding lumen tube into one lumen of the multi-lumen medial portion, the transition fixture including a guidewire transition guide that has (f) one guide tube for each of the multiple guidewires, each guide tube having a guide lumen with proximal and distal ends, the proximal end of the guide lumen being aligned with its corresponding lumen tube and the distal end of the guide lumen being aligned with its corresponding lumen in the multi-lumen medial portion, and (g) a transition guide web holding all of the guide tubes together; and each lumen of the multiple lumens other than the single output lumen is sized to match the corresponding guidewire passing therethrough.

2. The multi-lumen catheter of claim 1 wherein in the distal-end portion each lumen of the multiple lumens and the single-output lumen has its corresponding distal-end axis, and the distal-end axis of the single output lumen is substantially coincident with the distal-end axis of one of the multiple lumens when all of the distal-end axes are straight and mutually parallel.

3. The multi-lumen catheter of claim 1 wherein the guidewire transition guide is an integrally-formed component.

4. The multi-lumen catheter of claim 3 wherein the guidewire transition guide is made of polymer material.

5. The multi-lumen catheter of claim 3 wherein the guidewire transition guide is metallic.

6. The multi-lumen catheter of claim 1 wherein each lumen tube receives its corresponding guidewire through a corresponding guidewire entry-port fitting attached to each lumen tube and defining its corresponding entry port.

7. The multi-lumen catheter of claim 1 wherein one or more of the multiple guidewires each has multiple physical characteristics, and the physical characteristics of all of the guidewires are not the same.

8. The multi-lumen catheter of claim 7 wherein one or more of the multiple guidewires each has the physical characteristic of its diameter differing from the diameter of at least one other of the multiple guidewires.

9. The multi-lumen catheter of claim 8 wherein one or more of the multiple guidewires each has a differing stiffness from the stiffness of at least one other of the multiple guidewires.

10. The multi-lumen catheter of claim 1 wherein the single output lumen has a diameter and the taper of the tapered tip reduces the tapered tip diameter to substantially the diameter of the single output lumen.

11. The multi-lumen catheter of claim 1 wherein one of the multiple lumens, with its guidewire removed, is configured for fluid delivery to and through the tapered tip.

12. The multi-lumen catheter of claim 1 wherein each of the guidewires has a tip portion having a rest shape, and the rest shape of one or more of the guidewires is not substantially straight.

13. The multi-lumen catheter of claim 1 wherein at least one of the multiple lumens in the distal-end portion is surrounded by an encircling reinforcement.

14. The multi-lumen catheter of claim 1 wherein the distal-end portion includes at least one radio-opaque marker band.

15. In a multiple-lumen catheter configured to support multiple guidewires for treatment of vascular blockages, each of the multiple lumens being circular in cross-section and having a diameter, the catheter comprising a proximal-end assembly and an elongate tube including a multi-lumen medial portion and a distal-end portion therebeyond therebetween, the improvement wherein:

each of the multiple lumens is a single-guidewire lumen extending from its own guidewire entry port in the proximal-end assembly to a lumen convergence portion of the elongate tube;

the distal-end portion of the elongate tube includes (a) the lumen convergence portion along which the multiple lumens merge into a single output lumen being sized to match the largest-diameter lumen of the multiple lumens, (b) an intermediate distal-end section extending from the lumen convergence portion and surrounding the single output lumen continuing therethrough, and (c) a tapered tip at the end thereof and surrounding the single output lumen continuing therethrough;

the proximal end assembly includes (d) one lumen tube for each of the multiple lumens, each tube configured to receive a corresponding selected guidewire, and (e) a transition fixture configured to direct each selected guidewire from its corresponding lumen tube into one lumen of the multi-lumen medial portion and including a guidewire transition guide that has (f) one guide tube for each selected guidewire, each guide tube having a guide lumen with proximal and distal ends, the proximal end of the guide lumen being aligned with its corresponding lumen tube and the distal end of the guide lumen being aligned with its corresponding lumen in the multi-lumen medial portion, and (g) a transition guide web holding all of the guide tubes together; and each of the multiple lumens other than the single output lumen is sized to match the corresponding selected guidewire.

16. The multi-lumen catheter of claim 15 wherein in the distal-end portion each lumen of the multiple lumens and the single-output lumen has its corresponding distal-end axis, and the distal-end axis of the single output lumen is substantially coincident with the distal end axis of one of the multiple lumens when all of the distal-end axes are straight and mutually parallel.

17. The multi-lumen catheter of claim 15 wherein the single output lumen has a diameter and the taper of the tapered tip reduces the tapered tip diameter to substantially the diameter of the single output lumen.

* * * * *